United States Patent
Ishihara et al.

(10) Patent No.: US 8,394,995 B2
(45) Date of Patent: Mar. 12, 2013

(54) PROCESS FOR PREPARATION OF CARBONYL COMPOUND AND PRO-OXIDANT FOR PREPARATION OF CARBONYL COMPOUND

(75) Inventors: Kazuaki Ishihara, Nagoya (JP); Muhammet Uyanik, Nagoya (JP); Yukihiro Isogai, Nagoya (JP); Suguru Ohara, Nagoya (JP)

(73) Assignee: National University Corporation Nagoya University, Aichi (JP)

( * ) Notice: Subject to any disclaimer, the term of this patent is extended or adjusted under 35 U.S.C. 154(b) by 884 days.

(21) Appl. No.: 12/441,194

(22) PCT Filed: Aug. 29, 2008

(86) PCT No.: PCT/JP2008/065567
§ 371 (c)(1),
(2), (4) Date: Mar. 13, 2009

(87) PCT Pub. No.: WO2009/028676
PCT Pub. Date: Mar. 5, 2009

(65) Prior Publication Data
US 2010/0041917 A1 Feb. 18, 2010

(30) Foreign Application Priority Data
Aug. 31, 2007 (JP) ................ P2007-226843

(51) Int. Cl.
C07C 69/76 (2006.01)
C07C 45/29 (2006.01)
C07C 45/30 (2006.01)
(52) U.S. Cl. ........ 568/363; 568/342; 568/385; 568/404; 560/83
(58) Field of Classification Search ............ 568/342, 568/363, 385, 404; 560/83
See application file for complete search history.

(56) References Cited

FOREIGN PATENT DOCUMENTS
WO 2009/028676 3/2009

OTHER PUBLICATIONS

Muramoto et al., Chem. Abst. 89:59387.*
Nippon Kayaku Co. Ltd., Chem. Abst. 85:22780.*
Martin, G. Chem. Abst. 41:4742.*
Saz et al., Chem. Abst 37:37587.*
Barber et al., Chem. Abst. 22:27035.*
Boyle M. Chem. Abst. 4:8943.*
Dolenc et al. J. Org. Chem, 2006,71, 8028-8036.*
Koposov, et al., "Preparation and Reductive Decomposition of 2-Iodoxybenzenesulfonic Acid. X-ray Crystal Structure of 1-Hydroxy-1H-1,2,3-benziodoxathiole 3,3-Dioxide", Eur. J. Org. Chem., vol. 21 (2006) 4791-4795.
Zhdankin, et al., "Derivatives of 2-iodoxybenzenesulfonic acid: new pseudocyclic hypervalent iodine reagents", ARKIVOC, vol. iv (2005) 8-18.
Geoffroy, et al., "Chemoselective on-pot reductive deamination of aryl amines", Tetrahedron Letters, vol. 42, No. 32 (2001) 5367-69.
Cerfontain, et al., "On the positional reactivity order in the sulfur trioxide sulfonation of benzene, halogenobenzenes, halogenonaphthalenes, and chloroanthracenes", Can. J. Chem., vol. 72, No. 9 (1994) 1966-71.
Figuly, et al., "Ortho Lithiations of Arenesulfonic Acids. New Methodology for Electrophilic Aromatic Substitutions", J. Org. Chem., vol. 45, No. 18 (1980) 3728-29.
Justik, "Oxidative rearrangements of arylalkanones with 1H-1-hydroxy-5-methyl-1,2,3-benziodoxathiole 3,3-dioxide, a 'green' analog of Koser's reagent", Tetrahedron Letters, vol. 48, No. 17 (2007) 3003-07.
Thottumkara et al., Organic Letters, vol. 7, No. 14 (2005), 2933-36.
Schulze et al., Synthesis, No. 2 (2006), 257-60.
Annual Meeting on Chemical, The 87th Society of Japan in Spring (2007), Koen Yokoshu II, Mar. 12, 2007, p. 876 (1-C8-05).
Koposov et al., European Journal of Organic Chemistry, No. 21, (2006), 4791 to 95.
Annual Meeting on Chemical, The 88th Society of Japan in Spring (2008), Koen Yokoshu II, Mar. 12, 2008, p. 1325 (2J4-39).
Chau et al., The Anomalous Course of the Reduction of Diphenyl-2,2'-disulfonyl Chloride. An Old mystery Reexamined and Explained, The Journal of Organic Chemistry, vol. 42, No. 20 (1977), 3265-70.
Koser et al., Synthesis of 1H-1-(1-alkynyl)-5-methyl-1,2,3-benziodoxathiole 3,3-dioxides: Alkynyl(aryl)iodonium sulfonates with Heterocyclic iodine, The Journal of Organic Chemistry, vol. 58, No. 25 (1993), 7310-12.
More, et al., "A Simple and Advantageous Protocol for the Oxidation of Alcohols with o-Iodoxybenzoic Acid (IBX)", Organic Letters, vol. 4, No. 17 (2002) 3001-3.
Bulman Page, et al., "In Situ Generation of 2-Iodoxybenzoic Acid (IBX) in the Presence of Tetraphenylphosphonium Monoperoxysulfate (TPPP) for the Conversion of Primary Alcohols into the Corresponding Aldehydes", Synlett, No. 10 (2007) 1565-68.

Primary Examiner — Peter G O Sullivan
(74) Attorney, Agent, or Firm — Fitzpatrick, Cella, Harper & Scinto

(57) ABSTRACT

The invention provides a process for the preparation of a carbonyl compound in high efficiency by oxidizing an alcohol. The process for the preparation of a carbonyl compound of the present invention includes a step of oxidizing an alcohol in the presence of a compound of the formula (I) or a derivative or a salt thereof, and an oxidant, (I)

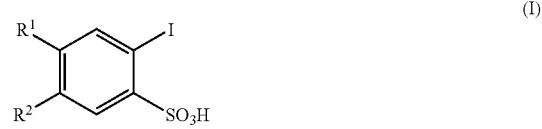

wherein $R^1$ and $R^2$ independently represent hydrogen, a halogen, a nitro or acidic group, or an alkyl or alkoxy group, each of which optionally has a substituent, or $R^1$ and $R^2$ combine the two carbon atoms to which they are boned to form an aromatic ring.

20 Claims, No Drawings

PROCESS FOR PREPARATION OF CARBONYL COMPOUND AND PRO-OXIDANT FOR PREPARATION OF CARBONYL COMPOUND

DESCRIPTION OF THE RELATED ART

Priority is claimed on Japanese Patent Application No. 2007-226843, filed Aug. 31, 2007, the content of which is incorporated herein by reference.

TECHNICAL FIELD

The present invention relates to a process for the preparation of a carbonyl compound and pro-oxidant for preparation of a carbonyl compound. More particularly, the present invention relates to pro-oxidant for the preparation of a carbonyl compound by oxidation of alcohol and the preparative process.

BACKGROUND ART

A carbonyl compound such as an aldehyde or a ketone is an extremely important material in organic synthesis. As the processes for the preparation, various types of the reactions have been known for a long time. Of the known synthetic processes, the preparative process by oxidation of alcohol can be nominated as a representative one. As a process of oxidation of alcohol, for example, the process applying heavy metal oxidants (such as a potassium permanganate, a bichromic acid and salt thereof, chromium trioxide), the dimethyl sulfoxide oxidation process (Swern Oxidation) or the process of oxidation (TPAP Oxidation) using a transition metal catalyst are known. In addition, the process of oxidation using 2-iodoxybenzoic acid, which is prepared from 2-iodobenzoic acid and 2 $KHSO_5 \cdot KHSO_4 \cdot K_2SO_4$ (Oxone (registered trademark)) as an oxidant, was known. For example, in Non-patent Document 1, a process for the oxidation of alcohol in the presence of 1 mol % of an 2-iodoxybenzoic acid derivative based on the alcohol, which was prepared on site from 2-iodobenzoic acid derivative and Oxone (registered trademark) as an oxidant, in nitromethane is disclosed.

Non-patent Document 1: Chemical Society of Japan No. 87 Spring Annual Meeting Presentation, Lecture Number 1C8-05*A.

DISCLOSURE OF THE INVENTION

However, the application of a heavy metal oxidant has an issue from the viewpoint of environmental consideration and a transition metal catalyst has an issue from the viewpoint of economic aspects because it is expensive. In addition, as the process of oxidation using a 2-iodoxybenzoic acid derivative, it is known that the yield is low because it is easy for a side reaction to occur in a mixture solvent of acetonitrile and water, or in a mixture of ethyl acetate and water. Furthermore, there is a problem for industrial application of nitromethane.

The aim of the present invention is to provide a process for the preparation of a carbonyl compound by oxidation of alcohol, in which a carbonyl compound can be obtained highly efficiently, even if the present invention uses a solvent which is easy to handle.

(1) The present invention provides a process for the preparation of a carbonyl compound, comprising a step of:
oxidizing an alcohol, in the presence of 2-iodobenzenesulfonic acid represented by the formula (I) or a derivative or a salt thereof, and an oxidant,

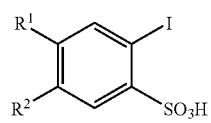

wherein $R^1$ and $R^2$ independently represent hydrogen, a halogen, a nitro or acidic group, or an alkyl or alkoxy group, each of which optionally has a substituent.

$R^1$ and $R^2$ combine the two carbon atoms to which they are boned to form an aromatic ring.

(2) The present invention provides a process for the preparation of a carbonyl compound according to (1),
wherein the alcohol is an alcohol of the formula (II)

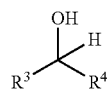

$R^3$ and $R^4$ are independently hydrogen; an alkyl, alkenyl, alkynyl, cycloalkyl, cycloalkenyl, aryl or a heteroaryl group; or an alkyl, alkenyl, alkynyl, cycloalkyl, cycloalkenyl, aryl or a heteroaryl group, each of which has a substituent, or $R^3$ and $R^4$ combine with the carbon to which they are bonded to form a cycloalkyl or cycloalkenyl group, and
the carbonyl compound is a carbonyl compound of the formula (III)

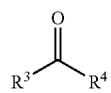

wherein $R^3$ and $R^4$ are defined as above.

(3) A process for the preparation of a carbonyl compound according to (1) or (2), wherein in the formula (I) $R^1$ is a hydrogen, and $R^2$ is an alkyl group having 1-4 carbon atoms.

(4) A process for the preparation of a carbonyl compound according to any one of (1) to (3), wherein in the formula (I) either $R^1$ or $R^2$ is hydrogen.

(5) A process for the preparation of a carbonyl compound according to any one of (1) to (4), wherein the oxidant is a peroxymonosulfuric acid salt.

(6) A process for the preparation of a carbonyl compound according to any one of (1) to (4), wherein the oxidant is a mixture of inorganic salts of potassium hydrogen peroxysulfate, potassium hydrogen sulfate, and potassium sulfate.

(7) A process for the preparation of a carbonyl compound according to any one of (1) to (6), wherein a dehydrating agent exists (8) A process for the preparation of a carbonyl compound according to (7), wherein the dehydrating agent is an anhydrous sodium sulfate (9) A process for the preparation of a carbonyl compound according to any one of (1) to (8), wherein the alcohol is the cyclic secondary alcohol with a 5-12 membered ring which may have a substituent, and the carbonyl compound is cyclic α,β-enone with 5-12 membered ring which may have a substituent.

(10) A pro-oxidant, comprising a 2-iodobenzenesulfonic acid of formula (I) or the derivative or the salt thereof.

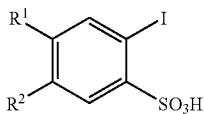 (I)

wherein $R^1$ and $R^2$ independently represent hydrogen, a halogen, a nitro or acidic group, or an alkyl or alkoxy group, each of which optionally has a substituent, or $R^1$ and $R^2$ combine the two carbon atoms to which they are boned to form an aromatic ring.

According to the present invention, even if the solvent is easy to handle, a carbonyl compound can be highly efficiently obtained by the process for preparation by oxidation of alcohol.

BEST MODE FOR CARRYING OUT THE INVENTION

One example of a process for the preparation of a carbonyl compound of the present invention is explained.

The process for the preparation of a carbonyl compound of the present example is a process for the preparation of a carbonyl compound having a step of oxidizing alcohol in the presence of a compound of the formula (I) (Compound (I) is as follows) and an oxidant.

<Carbonyl Compound>

As a carbonyl compound, a compound having a structure of the formula (1) can be used without any limitation in particular. The carbonyl compounds, such as compounds having a ketone, aldehyde or carboxyl group, can be used.

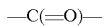 (1)

In addition, as a carbonyl compound, a carbonyl compound of the formula (III), for example, can be used.

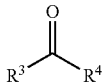 (III)

wherein $R^3$ and $R^4$ are independently hydrogen; an alkyl, alkenyl, alkynyl, cycloalkyl, cycloalkenyl, aryl or heteroaryl group; or an alkyl, alkenyl, alkynyl, cycloalkyl, cycloalkenyl, aryl or heteroaryl group, each of which has a substituent; or $R^3$ and $R^4$ combine with the carbon to which they are bonded to form a cycloalkyl or cycloalkenyl group.

In addition, as the carbonyl compound, a cyclic α,β-enone with a 5-12 member ring which may have a substituent can be used.

For example, a cycloenone of the formula (V) can be used.

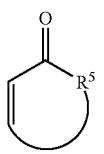 (V)

wherein $R^5$ is an alkylene, alkenylene, alkynylene group, or an alkylene, alkenylene, alkynylene group each of which has a substituent, but, $R^5$ combines with the three adjacent carbon atoms to form a 5-12 member ring.

<Compound (I)>

Compound (I) is a 2-iodobenzenesulfonic acid of the formula (I) or a derivative or salt thereof.

In formula (I), $R^1$ and $R^2$ independently represent hydrogen, a halogen, a nitro or acidic group, or an alkyl or alkoxy group, each of which optionally has a substituent, or $R^1$ and $R^2$ combine the two carbon atoms to which they are boned to form an aromatic ring.

The alkyl group in Compound (I) may be selected according to the solvent or the alcohol used in the oxidation without any limitation in particular. For example, an alkyl group having 1-8 carbon atoms, such as a methyl, ethyl, n-propyl, an isopropyl, an n-butyl, an isobutyl, a sec-butyl, or a tert-butyl group can be used.

The alkoxy group may be selected by considering the solvent or the alcohol used in the oxidation without any limitation in particular. For example, a alkoxy having 1-8 carbon atoms, such as a methoxy group, an ethoxy group, an n-propoxy group, an isopropoxy group, an n-butoxy group, an iso-butoxy group, a sec-butoxy group, a tert-butoxy group, an n-pentoxy group, an isopentoxy group, a neopentoxy group, an n-hexyloxy group, or an n-octyloxy group can be used.

The substituents in the alkyl or alkoxy group are not limited in particular. For example, they may be a halogen, and the number of the substituents may be 1-3.

The aromatic ring which $R^1$ and $R^2$ combine with the two carbon atoms to which they are bonded to form, such as a benzene ring, can be used without any limitation in particular.

A halogen means any one of fluorine, chlorine, bromine and iodine.

An acidic group, such as, a carboxylic acid group, and a sulfonic acid group can be used without any limitation in particular.

The combination of $R^1$ and $R^2$ need not be limited in particular, and any one of the arbitrary combinations can be selected. Of all the arbitrary combinations, it is preferable that the combination of $R^1$ being hydrogen and $R^2$ being an alkyl group with 1-8 carbon atoms, or the combination of both of $R^1$ and $R^2$ being hydrogen. As a Compound (I) satisfying the above requirement, 2-iodobenzenesulfonic acid or a 2-iodo-5-methylbenzenesulfonic acid, for example, can be used.

As the salt of 2-iodobenzenesulfonic acid or the derivative thereof, for example, a salt of alkaline metal such as sodium, potassium, or lithium salt; or a salt of an alkaline earth metal such as magnesium or calcium salt can be used. Of them, sodium or calcium salt is preferable.

The salt of 2-iodobenzenesulfonic acid or the derivative thereof can be prepared according to the method disclosed in J. Org. Chem., (1993), Vol. 58 (No. 25), 7310-7312. Alternatively, it can be prepared by steps of mixing 2-iodobenzenesulfonic acid or the derivative thereof and the aqueous solution such as sodium hydroxide or potassium hydroxide solution, and carrying out suitable purification.

One kind of Compound (I) may be used alone, or combinations of two or more kinds of Compound (I) may be used.

Compound (I) is used in a quantity which is not limited in particular. However, the oxidation rate become fast if the quantity is 0.001 mol % or more based on alcohol as the starting material of oxidation. Five mol % or less is preferable from the economic viewpoint that the purification after the reaction becomes easy. Thus, it is preferable to use Compound (I) in the quantity of 0.001-5 mol % based on the alcohol, and 0.01-2 mol % is more preferable, 0.05-1 mol % is most preferable.

<Oxidant>

As the oxidant, an inorganic oxidant or organic oxidant may be used without limitation in particular as long as it can oxidize the iodine of Compound (I) to a 5-valent one. Specially, as the inorganic oxidation, a peroxymonosulfuric acid salt such as potassium peroxymonosulfate, sodium peroxydisulfate ($Na_2S_2O_8$), or potassium peroxydisulfate ($K_2S_2O_8$) can be used. As the organic oxidant, a hydroperoxide such as hydrogen peroxide or tert-butylhydroperoxide can be used. Of the above-mentioned oxidants to be used, potassium peroxymonosulfate is preferable. In addition, the inorganic salt mixture of 2 $KHSO_5.KHSO_4.K_2SO_4$ is preferable from the viewpoint of high oxidation ability, with little side reaction, and easiness in the handling. As the oxidant, Oxone (registered trademark) ($2KHSO_5.KHSO_4.K_2SO_4$) can be used.

The oxidants can be used individually or 2 or more kinds of oxidants can be used together.

According to the oxidant type, there is an oxidant which can oxidize 1 molar hydroxyl groups of alcohol with 1 molar oxidant, or an oxidant which can oxidize 2 molar hydroxyl groups of alcohol with 1 molar oxidant. In the present invention, the quantity of the oxidant which can oxidize 1 molar hydroxyl group is defined as oxidation chemical equivalent of the oxidant. The quantity of the oxidant to be used is not limited in particular. However, 1 to 6 oxidation chemical equivalents are preferable since oxidation rate is increased when 1 or more oxidation chemical equivalents of oxidant is used, and the side reaction is reduced when 6 oxidation chemical equivalents or less are used. Thus, it is preferable to use an oxidant in the quantity of 1-6 oxidation chemical equivalents based on alcohol, and 1.6-4 oxidation chemical equivalents or more is preferable.

For example, when Oxone (registered trademark) (2 $KHSO_5.KHSO_4.K_2SO_4$ Mw: 614.7) is used as an oxidant, the oxidation chemical equivalent of Oxone (registered trademark) is 307.4 g/(oxidation chemical equivalent). The quantity of Oxone (registered trademark) to be used is not limited in particular, but 1 to 6 oxidation chemical equivalents are preferable, since the oxidation rate increases when one oxidation chemical equivalent (0.5 mol) or more is used based on 1 molar hydroxyl group of alcohol as a starting material of the oxidation, and a side reaction is reduced when six oxidation chemical equivalents (3 mol) or less are used. Thus, as the amount of the oxidant to be used, 1-6 oxidation chemical equivalents (0.5-3 mol) based alcohol are preferable, and 1.6-4 oxidation chemical equivalents (0.8-2 mol) are more preferable.

<Alcohol>

The alcohol can be selected according to the carbonyl compound which is the resulting material of the preparation, without any limitation in particular. A mono-valent alcohol can be used, and a 2-, 3- or 4-valent or more alcohol can be used, too. In addition, any one of a primary alcohol and a secondary alcohol can be used.

When the alcohol is represented in R—OH, the kinds or structures of R are not limited in particular. For example, as the kind of R, it can be an alkyl group, an alkenyl group, an alkynyl group or an aralkyl group.

The number of carbon atoms in the above-mentioned alkyl group, alkenyl group, alkyny group or aralkyl group is generally 1-20, and is more preferably 1-10. In addition, the alkyl group, alkenyl group, alkynyl group and aralkyl group may be a straight-chain, a branched chain or a cyclic chain, or may have a side chain.

For example, as the alkyl group, a methyl group, an ethyl group, an n-propyl group, an isopropyl group, a butyl group, an isobutyl group, a sec-butyl group, a tert-butyl group, a pentyl group, an isopentyl group, a neopentyl group, a hexyl group, heptyl group, an octyl group, a nonyl group, a decyl group can be used.

For example, as the alkenyl group, a vinyl group, an allyl group, a 1-propenyl group, a butenyl group, a pentenyl group, a hexenyl group, a heptenyl group, an octenyl group, a nonenyl group, or a decenyl group can be used without any limitation in particular.

For example, as the alkynyl group, an ethynyl group, a propynyl group, a butynyl group, a pentynyl group, a hexenyl group, a pentynyl group, an octinyl group, a nonynyl group, and a decynyl group can be used without any limitation in particular.

As the aralkyl group, the above-mentioned alkyl groups which are substituted by an aryl group at any one of places can be used without any limitation in particular. In general, an aralkyl group having 7-16 carbon atoms can be used, such as, for example, a benzyl group, a phenethyl group, a phenyl propyl group, a phenyl butyl group, a phenyl pentyl group, a phenyl hexyl group, a phenyl heptyl group, a phenyl octyl group, a phenyl nonyl group, a phenyl decyl, a naphthyl methyl group, a naphthyl ethyl group, a naphthyl propyl group, a naphthyl butyl group, a naphthyl pentyl group, a naphthyl hexyl group, an anthryl methyl group, and an anthryl ethyl group can be used. On the other hand, as the above-mentioned aryl group, an aryl group have 6-14 carbon atoms, such as, for example, a phenyl group, a naphthyl group, an azulenyl group, and an anthryl group can be used.

For example, as the cyclic group, a cyclopropyl group, a cyclobutyl group, a cyclopentyl group, a cyclohexyl group, a cycloheptyl group, a cyclooctyl group, a norbonyl group, and a tricyclodecanyl group are given without it being limited for annular group in particular.

As a side-chain of the rings, the above-mentioned alkyl group, alkenyl group, alkynyl group or aralkyl group, as well as a cyclic acetal group and a silyloxy group which may have a substituent can be used, without any limitation in particular. As a cyclic acetal group, for example, —O—$(CH_2)_n$—O— is illustrated, wherein n shows 1-4 integers. As a substituent of the cyclic acetal group, the above-mentioned alkyl groups can be used. As the silyloxy group which may have a substituent, a triethylsilyloxy group, or a tert-butyldimethylsilyloxy group can be used.

In addition, as the alcohol, an alcohol of the formula (II)

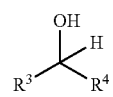

(II)

wherein $R^3$ and $R^4$ are independently hydrogen; an alkyl, alkenyl, alkynyl, cycloalkyl, cycloalkenyl, aryl or heteroaryl group; or an alkyl, alkenyl, alkynyl, cycloalkyl, cycloalkenyl, aryl or heteroaryl group, each of which has a substituent, or $R^3$ and $R^4$ combine with the carbon to which they are bonded to form a cycloalkyl or cycloalkenyl group.

When $R^3$ and $R^4$ as defined above are alkyl, they generally represent a straight-chain or branched hydrocarbon group having from 1 to 18 carbon atoms that is optionally substituted with from 1 to 8 identical or different substituent. The alkyl group preferably represents a straight-chain or branched hydrocarbon group having from 1 to 10 carbon atoms that is optionally substituted by from 1 to 3 identical or different substituents. More preferably, an alkyl group represents a methyl group, an ethyl group, an n-propyl group, an isopropyl group, a butyl group, an isobutyl group, a sec-butyl group, a tert-butyl group, a pentyl group, an isopentyl group, a neo-pentyl group, a hexyl group, a heptyl group, an octyl group, a nonyl group, or a decyl group.

When $R^3$ and $R^4$ as defined above are alkenyl groups, they generally represent a straight-chain or branched hydrocarbon group having from 2 to 18 carbon atoms that is optionally substituted with from 2 to 8 identical or different substituents. The alkenyl group preferably represents a straight-chain or branched hydrocarbon group having from 2 to 10 carbon atoms that is optionally substituted by from 2 to 3 identical or different substituents. More preferably, the alkenyl group represents a vinyl group, an allyl group, a 1-propenyl group, a butenyl group, a pentenyl group, a hexenyl group, a heptenyl group, an octenyl group, a nonenyl group, or a decenyl group.

When $R^3$ and $R^4$ as defined above are an alkynyl group, they generally represent a straight-chain or branched hydrocarbon group having from 2 to 18 carbon atoms that is optionally substituted by from 2 to 8 identical or different substituents. For example, as the alkynyl group, an ethynyl group, a propynyl group, a butynyl group, a pentynyl group, a hexynyl group, a heptynyl group, an octinyl group, a nonynyl group, or a decynyl group can be used, without any limitation in particular.

When $R^3$ and $R^4$ as defined above are a cycloalkyl group, they generally represent a straight-chain or branched cyclic hydrocarbon group having from 5 to 18 carbon atoms that is optionally substituted by from 1 to 8 identical or different substituents and in which one or more $CH_2$ groups of the cycloalkyl group can be replaced by oxygen. The cycloalkyl group preferably contains from 5 to 10 carbon atoms (more preferably cyclohexyl) in which again one or more $CH_2$ group of the cycloalkyl group can be replaced by one or more oxygen.

When $R^3$ and $R^4$ as defined above are a cycloalkenyl group, they generally represent a cyclic hydrocarbon group having from 5 to 18 carbon atoms that is optionally substituted by from 1 to 8 identical or different substituents and in which one or more $CH_2$ groups of the cycloalkyl group can be replaced by oxygen. The cycloalkenyl group preferably contains 5 to 10 carbon atoms (more preferably cyclohexenyl) in which again one or more $CH_2$ group of the cycloalkenyl group can be replaced by one or more oxygen.

When $R^3$ and $R^4$ as defined above are an aryl group, they generally represent a aromatic group having from 6 to 14 carbon atoms (preferably from 6 to 10 carbon atoms) that is optionally substituted by from 1 to 8 identical or different substituents and is optionally fused (particularly phenyl or naphthyl that is optionally substituted by from 1 to 3 identical or different substituent, preferably phenyl, p-methylphenyl, or p-methoxyphenyl group).

When $R^3$ and $R^4$ as defined above are an heteroaryl group, they generally represent a aromatic group having from 6 to 14 carbon atoms (preferably from 5 to 10 carbon atoms, particularly from 5 to 7 carbon atoms) and from 1 to 3 (preferably 1 or 2) heteroatoms selected from the group consisting of N, O and S that is optionally substituted by from 1 to 8 identical or different substituents and is optionally fused (most preferably furan or thiophene).

When $R^3$ and $R^4$ combine with the carbon atom to which they bonded to form a cyclic group, as the cyclic group, a cycloalkyl group, a cycloalkenyl group, an aryl group or a heteroaryl group can be used, without any limitation in particular, For example, particularly a cyclopropyl group, a cyclobutyl group, a cyclopentyl group, a cyclohexyl group, cycloheptyl group, cyclooctyl group, norbonyl group, tricyclodecanyl group can be used.

The alkyl group, the alkenyl group, the alkynyl group, the cycloalkyl group, the cycloalkenyl group, the aryl group, a heteroaryl group or the cyclic group are each optionally substituted with from 1 to 8 identical or different substituents selected from the group consisting of alkyl, alkenyl, alkynyl, CN, COOH, COO-alkyl, COO-aryl, CO-alkyl, CO-aryl, O-alkyl, O-aryl, O—CO-aryl, O—CO-alkyl, OCOO-alkyl, NO, $NO_2$, NOH, aryl, fluorine, chlorine, bromine, iodine, $NO_2$, $Si(alkyl)_3$, CHO, $SO_3H$, $SO_3$-alkyl, $SO_2$-alkyl, SO-alkyl, $CF_3$, NHCO-alkyl, $CONH_2$, CONH-alkyl, NHCOH, NHCOO-alkyl, $CHCHCO_2$-alkyl, and $CHCHCO_2H$. In addition, they may be substituted with a chain acetal group such as dimethylacetal, or diethyl acetal, the cyclic acetal group which may have a substituent, or silyloxy group. The cyclic acetal group may be —O—$(CH_2)_n$—O—, wherein, n shows 1-4 integers. The substituent of the cyclic acetal group may be the above-mentioned groups such as alkyl group. The silyloxy group may have a substituent of, for example, a triethylsilyloxy group, or a tert-butyldimethylsilyloxy group.

The compounds of the formula (II) can be used individually or in any desired mixture.

In addition, as the alcohol, a second cyclic alcohol with a 5-12 member ring which may have a substituent can be used.

For example, the cyclic secondary alcohol of the formula (I V) can be used.

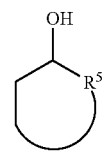

(IV)

wherein $R^5$ represents an alkylene, alkenylene, or alkynylene group, or an alkylene, alkenylene, or alkynylene group each of which may have a substituent, but $R^5$ combines with the three carbon atoms to which they are boned to form a 5-12 member ring.

When $R^5$ as defined above is an alkylene group, it generally represents a straight-chain or branched hydrocarbon group having from 2 to 18 carbon atoms that is optionally substituted by from 1 to 8 identical or different substituents. The alkylene group preferably represents a straight-chain or branched hydrocarbon group having from 2 to 10 carbon atoms that is optionally substituted with from 1 to 3 identical or different substituents. More preferably, the alkylene group represents ethylene, an n-propylene group, a butylene group, a pentylene group, a hexylene group, a heptylene group, an octylene group, or a nonylene group.

When $R^5$ as defined above is an alkenylene group, it generally represents a straight-chain or branched hydrocarbon group having from 2 to 18 carbon atoms that is optionally substituted with from 1 to 8 identical or different substituents. An alkenylene group preferably represents a straight-chain or branched hydrocarbon group having from 2 to 10 carbon atoms that is optionally substituted with from 1 to 3 identical or different substituents. More preferably, a vinylene group, an allylene group, a 1-propenylene group, a butenylene group, a pentenylene group, a hexenylene group, a heptenylene group, an octenylene group, or a nonenylene group can be used.

When $R^5$ as defined above is an alkynylene group, it generally represents a straight-chain or branched hydrocarbon group having from 2 to 18 carbon atoms that is optionally substituted with from 2 to 8 identical or different substituents. An alkynylene group preferably represents a straight-chain or branched hydrocarbon group having from 2 to 10 carbon atoms that is optionally substituted with from 1 to 3 identical or different substituents.

For example, as an alkynylene group, an ethynylene group, a propynylene group, a butynylene group, a pentynylene group, a hexynylene group, a heptynylene group, an octynylene group, or a nonynylene group can be used, without any limitation in particular. The alkylene group, an alkenylene group, or an alkynylene group are each optionally substituted with from 1 to 8 identical or different substituents selected from the group consisting of alkyl, alkenyl, alkynyl, CN, COOH, COO-alkyl, COO-aryl, CO-alkyl, CO-aryl, O-alkyl, O-aryl, O—CO-aryl, O—CO-alkyl, OCOO-alkyl, NO, $NO_2$, NOH, aryl, fluorine, chlorine, bromine, iodine, $NO_2$, $Si(alkyl)_3$, CHO, $SO_3H$, $SO_3$-alkyl, $SO_2$-alkyl, SO-alkyl, $CF_3$, NHCO-alkyl, $CONH_2$, CONH-alkyl, NHCOH, NHCOO-alkyl, $CHCHCO_2$-alkyl, and $CHCHCO_2H$. In addition, they may be substituted with a chain acetal group such as dimethylacetal, or diethyl acetal, a cyclic acetal group which may have substituent, or a silyloxy group. As the cyclic acetal group, it may be —O—$(CH_2)_n$—O—, wherein n shows 1-4 integers. As the substituent of the cyclic acetal group, an above-mentioned group such as an alkyl group, may be used. As the silyloxy group which may have a substituent, for example, a triethylsilyloxy group, or tert-butyldimethylsilyloxy group may be used.

<Solvent>

The solvent is not limited in particular. For example, an ester solvent such as ethyl acetate, a nitrile solvent such acetonitrile, a halogen solvent such as 1,2-dichloroethane, an aromatic solvent such as benzene, a ketone solvent such as acetone, an ether type solvent such as dioxane, or a nitroalkane solvent such as nitromethane can be used. For example, from the viewpoint of ease of handling, preferably ethyl acetate or acetonitrile is used.

The solvent can be used individually or in any desired mixture of 2 or more kinds of solvents.

<Dehydrating Agent>

A dehydrating agent is not limited in particular, and preferably anhydrous sodium sulfate, anhydrous potassium sulfate, anhydrous calcium sulfate, or anhydrous magnesium sulfate can be used. Of them, the dehydrating agent to be used is preferably anhydrous sodium sulfate.

In addition, the dehydrating agent can be used individually or two or more kinds of dehydrating agents can be used together.

A dehydrating agent can be used in a quantity with no limitation in particular, as long as it can remove generating water. Preferably, a dehydrating agent can be used in a quantity of 1-10 mol (more preferably, 2-5 mol) chemical equivalent based on the 1 molar alcohol as the starting material of the oxidation.

<Preparative Process>

The process of the invention is not limited in particular as long as it includes the step of oxidizing an alcohol in the presence of Compound (I) and an oxidant, and an existing method can be used. For example, the oxidizing process (Oxidation reaction step) which includes steps of mixing Compound (I), oxidant and alcohol in the above-mentioned solvent, and heating resulting mixture liquid, can be used. Then the material, including the resulting carbonyl compound, can be obtained by separating the Compound (I) and the compound resulted from the oxidant from the cooled mixture liquid, and then removing the solvent (Removing step). In addition, when the alcohol is a primary alcohol, as the resulting carbonyl compound, a compound having an aldehyde group or carboxyl group can be expected. In this case, the primary alcohol can be oxidized to a compound having a carboxyl group, or can be selectively oxidized to a compound having an aldehyde group by using the above-mentioned dehydrating agent, if necessary.

The oxidation reaction is preferably carried out at temperature of 20° C. or higher, since the reaction rate increases at this temperature, and at temperature of 100° C. or lower, from the view point of preparation condition. Thus, the heating temperature is preferably 20-100° C., more preferably 30-100° C., and most preferably 40-90° C.

In addition, the heating time is not limited in particular, but it is preferably 30 minutes or more, since the reaction progresses, and 24 hours or less from the viewpoint of reaction efficiency. Thus, it is preferable that the heating time is from 30 minutes to 24 hours, and more preferably from 30 minutes to 12 hours.

The apparatus to be used for the above-mentioned heating step is not limited particularly, as long as it can heat the reaction system to the desired temperature. Existing apparatus can be used.

In addition, the reaction time can be shortened by using a powdered oxidant.

In the Removing step, the method for removing Compound (I), a compound resulted from an oxidant, or solvent is not limited particularly, and an existing technique can be used. For example, a process for obtaining the material containing a carbonyl compound, which includes steps of removing an insoluble substance in a mixture by filtering the mixture liquid after cooling, and then removing the solvent from the obtained filtrate by evaporation can be used.

The apparatus to be used for the filtering step is not limited particularly, and an existing apparatus can be used. In addition, the apparatus for removing the solvent is also not limited particularly, and an existing apparatus can be used.

The pro-oxidant of the present invention is used to improve the oxidation ability, and its effect can be shown by using little oxidant together. The condition using the pro-oxidant can be selected according to the condition described in the explanation of the preparative process of the present invention.

In addition, the cycloenone compounds of the formula (V) can be prepared from a cyclic secondary alcohol of the formula (IV), under some reaction conditions, for example, in the presence of 2-iodobenzenesulfonic acid of the formula (I) or the derivative or the salt thereof in a quantity which is more than the above-mentioned preferable quantity, and the oxidant in a quantity which is more than the above-mentioned preferable quantity. Particularly, when $R^5$ of the formula (IV) is an alkylene group which may have a substituent, the compound of the formula (IV) represents a cyclic alkanol, from which cyclic α,β-enone compounds can be prepared.

For example, 2-iodobenzenesulfonic acid or the derivative or salt thereof can be used preferably in a quantity of generally 1-10 mol % based on alcohol of the formula (IV) as a staring material, more preferably 3-8 mol %, and most preferably 4-6 mol %.

For example, the oxidant can be used in a preferable quantity of 2-8 oxidation chemical equivalents, more preferably 3-7 oxidation chemical equivalents, or most preferably 4-6 oxidation chemical equivalents, based on alcohol of equation (IV) as a starting material of oxidation.

In addition, preferably, the oxidant is Oxone (registered trademark) (2 $KHSO_5.KHSO_4.K_2SO_4$). When Oxone (registered trademark) is used, preferably, Oxone (registered trademark) can be used in a quantity of 2-8 oxidation chemical equivalent (1-4 mol), more preferably, 3-7 oxidation chemical equivalent (1.5-3.5 mol), or most preferably, 4-6 oxidation chemical equivalent (2-3 mol), based on 1 molar hydroxyl of the alcohol of the formula (IV) as the starting material of oxidation.

As the solvent, for example, nitromethane is preferable.

EXAMPLE

The following examples serve to elucidate the process of the invention, without restricting it either in spirit or scope.

Preparation Example 1

Preparation of 2-iodobenzenesulfonic acid

2-Iodobenzenesulfonic acid was prepared according to the method disclosed in J. Org. Chem., (1977), Vol. 42 (No. 20), 3265-3270 and J. Org. Chem., (1993), Vol. 58 (No. 25), 7310-7312.

Preparation Example 2

Preparation of 2-iodo-5-methylbenzenesulfonic acid

2-Iodo-5-methylbenzenesulfonic acid was prepared according to the method disclosed in J. Org. Chem., (1993), Vol. 58 (No. 25), 7310-7312.

Preparation Example 3

Preparation of 2-iodo-5-methylbenzoic acid

2-Iodo-5-methylbenzoic acid was prepared according to the method disclosed in Katritzky et al., Organic Preparations and Procedures Int. 1989, 21 (2), 157-162.

Preparation Example 4

Preparation of sodium 2-iodobenzenesulfonate

Sodium 2-iodobenzenesulfonate was prepared according to the method disclosed in J. Org. Chem., (1993), Vol. 58 (No. 25), 7310-7312.

Example 1

8.5 mg (0.03 mmol) of 2-iodobenzenesulfonic acid prepared by Preparation Example 1, 1.48 g (2.4 mmol) of Oxone (registered trademark) and 433 mg (3 mmol) of 5-nonanol were added to 3.75 ml ethyl acetate, and the mixture was heated at 70° C. while being stirred for ten hours. After heating, the mixture was cooled to room temperature, and the insoluble substance was removed by means of filtering. The obtained filtrate was vacuum-concentrated, and diethyl ether is added in the residue, and then an insoluble material was removed by filtering. The obtained filtrate was vacuum-concentrated, and then 5-nonanone was obtained. The yield of the obtained 5-nonanone was determined and the result is shown in Table 1.

Example 2

8.9 mg (0.03 mmol) of 2-iodo-5-methylbenzenesulfonic acid prepared by Preparation Example 2, 1.48 g (2.4 mmol) of Oxone (registered trademark) and 433 mg (3 mmol) of 5-nonanol were added in 3.75 ml of acetonitrile, and the mixture was heated at 70° C. while being stirred for three hours. The later treatment was carried out in the same way as in Example 1, and then 5-nonanone was obtained. The yield of the obtained 5-nonanone was determined and the result is shown in Table 1.

Example 3

1.8 mg (0.006 mmol) of 2-iodo-5-methylbenzenesulfonic acid, prepared by Preparation Example 2, 1.11 g (1.8 mmol) of powdered Oxone (registered trademark) and 433 mg (3 mmol) of 5-nonanol were added in 3.75 ml of nitromethane, and the mixture was heated at 70° C. while being stirred for seven hours. The later treatment was carried out in the same way as in Example 1, and then 5-nonanone was obtained. The yield of the obtained 5-nonanone was determined and the result is shown in Table 1.

Example 4

1.7 mg (0.006 mmol) of 2-iodobenzenesulfonic acid, prepared by Preparation Example 1, 1.11 g (1.8 mmol) of powdered Oxone (registered trademark) and 433 mg (3 mmol) of 5-nonanol were added to 3.75 ml of nitromethane, and the mixture was heated at 70° C. while being stirred for 7.5 hours. The later treatment was carried out in the same way as in Example 1, and then 5-nonanone was obtained. The yield of the obtained 5-nonanone was determined and the result is shown in Table 1.

Example 5

8.9 mg (0.03 mmol) of 2-iodo-5-methylbenzenesulfonic acid, prepared by Preparation Example 2, 2.04 g (3.3 mmol) of powdered Oxone (registered trademark) and 324 mg (3 mmol) of benzyl alcohol were added to 3.75 ml acetonitrile, and the mixture was heated at 70° C. while being stirred for one hour. The later treatment was carried out in the same way as in Example 1, and then benzaldehyde was obtained. The yield of the obtained benzaldehyde was determined and the result is shown in Table 1.

Example 6

8.9 mg (0.03 mmol) of 2-iodo-5-methylbenzenesulfonic acid prepared by Preparation Example 2, 1.48 g (2.4 mmol) of powdered Oxone (registered trademark) and 367 mg (3 mmol) of 1-phenylethanol were added to 3.75 ml of acetonitrile, and the mixture was heated at 70° C. while being stirred for one hour. The later treatment was carried out in the same way as in Example 1, and then acetophenone was obtained. The yield of the obtained acetophenone was determined and the result is shown in Table 1.

Example 7

8.9 mg (0.03 mmol) of 2-iodo-5-methylbenzenesulfonic acid prepared by Preparation Example 2, 2.04 g (3.3 mmol) of powdered Oxone (registered trademark) were added to 3.75 ml of nitromethane, and 450 mg (3 mmol) of 4-phenylbutanol was added dropwise for two hours, and the mixture was heated at 70° C. while being stirred for six hours. The later treatment was carried out in the same way as in Example 1, and then 4-phenylbutanoic acid was obtained. The yield of the obtained 4-phenylbutanoic acid was determined and the result is shown in Table 1.

Example 8

9.2 mg (0.03 mmol) of sodium 2-iodobenzenesulfonate prepared by Preparation Example 4, 1.48 g (2.4 mmol) of Oxone (registered trademark) and 433 mg (3 mmol) of 5-nonanol were added to 3.75 ml of acetonitrile, and the mixture was heated at 70° C. while being stirred for three hours. The later treatment was carried out in the same way as in Example 1, and then 5-nonanone was obtained. The yield of the obtained 5-nonanone was determined and the result is shown in Table 1.

Example 9

6.1 mg (0.02 mmol) of sodium 2-iodobenzenesulfonate prepared by Preparation Example 4, 0.37 g (0.6 mmol) of powdered Oxone (registered trademark), 0.5 g (3.5 mmol) of anhydrous sodium sulfate and 150 mg (1 mmol) of 4-phenyl butanol were added to 5 ml of nitromethane and the mixture was heated at 70° C. while being stirred under a nitrogen for two hours. The later treatment was carried out as the same as Example 1, and then 4-phenylbutanol was obtained. The yield of the obtained 4-phenylbutanal was determined and the result is shown in Table 2. (Yield 91%)

Example 10

6.1 mg (0.02 mmol) of sodium 2-iodobenzenesulfonate prepared by Preparation Example 4, 0.37 g (0.6 mmol) of powdered Oxone (registered trademark), 0.5 g (3.5 mmol) of anhydrous sodium sulfate and 154 mg (1 mmol) of (E)-3,7-dimethylocta-2,6-dien-1-ol were added to 5 ml of nitromethane, and the mixture was heated at 70° C. while being stirred under a nitrogen for two hours. The later treatment was carried out in the same way as in Example 1, and then (E)-3,7-dimethylocta-2,6-dienal was obtained. The yield of the obtained (E)-3,7-dimethylocta-2,6-dienal was determined and the result is shown in Table 2. (Yield: E:Z=16:1)

Example 11

6.1 mg (0.02 mmol) of sodium 2-iodobenzenesulfonate prepared by Preparation Example 4, 0.37 g (0.6 mmol) of powdered Oxone (registered trademark), 0.5 g (3.5 mmol) of anhydrous sodium sulfate and 156 mg (1 mmol) of octa-7-en-1-ol were added to 5 ml of nitromethane, and the mixture was heated at 70° C. while being stirred under a nitrogen for two hours. The later treatment was carried out in the same way as in Example 1, and then octa-7-enal was obtained. The yield of the obtained octa-7-enal was determined and the result is shown in Table 2. (Yield 92%)

Example 12

6.1 mg (0.02 mmol) of Sodium 2-iodobenzenesulfonate prepared by Preparation Example 4, 0.37 g (0.6 mmol) of powdered Oxone (registered trademark), 0.5 g (3.5 mmol) of anhydrous sodium sulfate, and 268 mg (1 mmol) of (Z)-octadeca-9-en-1-ol were added to 5 ml of nitromethane, and the mixture was heated at 70° C. while being stirred under a nitrogen for two hours. The later treatment was carried out in the same way as in Example 1, and then (Z)-olealdehyde was obtained. The yield of the obtained (Z)-olealdehyde was determined and the result is shown in Table 2. (Yield 90%)

Example 13

6.1 mg (0:02 mmol) of sodium 2-iodobenzenesulfonate prepared by Preparation Example 4, 0.49 g (0.8 mmol) of powdered Oxone (registered trademark), 0.5 g (3.5 mmol) of anhydrous sodium sulfate and 200 mg (1 mmol) of 3,3-dimethyl-1,5-dioxaspiro[5.5]undecan-9-ol were added to 5 ml of ethyl acetate, and the mixture was heated at 70° C. while being stirred under a nitrogen for eight hours. The later treatment was carried out in the same way as in Example 1, and then 3,3-dimethyl-1,5-dioxaspiro[5.5]undecan-9-one was obtained. The yield of the obtained 3,3-dimethyl-1,5-dioxaspiro[5.5]undecan-9-one was determined and the result is shown in Table 2. (Yield 91%)

Example 14

6.1 mg (0.02 mmol) of sodium 2-iodobenzenesulfonate prepared by Preparation Example 4, 0.49 g (0.8 mmol) of powdered Oxone (registered trademark), 0.5 g (3.5 mmol) of anhydrous sodium sulfate and 158 mg (1 mmol) of 1,4-dioxaspiro[4.5]decan-8-ol were added to 5 ml of ethyl acetate, and the mixture was heated at 70° C. while being stirred under a nitrogen for eight hours. The later treatment was carried out in the same way as in Example 1, and then 1,4-dioxaspiro[4.5]decane-8-one was obtained. The yield of the obtained 1,4-dioxaspiro[4.5]decane-8-one was determined and the result is shown in Table 1. (Yield 86%)

Example 15

6.1 mg (0.02 mmol) of sodium 2-iodobenzenesulfonate prepared by Preparation Example 4, 0.49 g (0.8 mmol) of powdered Oxone (registered trademark), 0.5 g (3.5 mmol) of anhydrous sodium sulfate and 230 mg (1 mmol) of 4-(triethylsilyloxy)cyclohexanol were added to 5 ml of ethyl acetate, and the mixture was heated at 70° C. while being stirred under a nitrogen for eight hours. The later treatment was carried out in the same way as in Example 1, and then 4-(triethylsilyloxy) cyclohexanone was obtained. The yield of the obtained 4-(triethylsilyl oxy)cyclohexanone was determined and the result is shown in Table 2. (Yield 74%)

Example 16

6.1 mg (0.02 mmol) sodium 2-iodobenzenesulfonate prepared by Preparation Example 4, 0.49 g (0.8 mmol) of powdered Oxone (registered trademark), 0.5 g (3.5 mmol) of anhydrous sodium sulfate and 232 mg (1 mmol) of 6-(tert-butyldimethylsilyloxy)hexan-2-ol were added to 5 ml of ethyl acetate, and the mixture was heated at 70° C. while being stirred under a nitrogen for seven hours. The later treatment was carried out in the same way as in Example 1, and then 6-(tert-butyldimethylsilyloxy)hexan-2-one was obtained. The yield of the obtained 6-(tert-butyldimethylsilyloxy)hexan-2-one was determined and the result is shown in Table 2. (Yield 90%)

Example 17

6.1 mg (0.02 mmol) of sodium 2-iodobenzenesulfonate prepared by Preparation Example 4, 0.49 g (0.8 mmol) of powdered Oxone (registered trademark), 0.5 g (3.5 mmol) of anhydrous sodium sulfate and 152 mg (1 mmol) of 3-methyl-5-(prop-1-en-2-yl)cyclohexa-2-enol were added to 5 ml of ethyl acetate, and the mixture was heated at 70° C. while being stirred under a nitrogen for eight hours. The later treatment was carried out in the same way as in Example 1, and then 3-methyl-5-(prop-1-en-2-yl)cyclohexa-2-enone was obtained. The yield of the obtained 3-methyl-5-(prop-1-en-2-yl)cyclohexa-2-enone was determined and the result is shown in Table 2. (Yield 91%)

Comparative Example 1

7.86 mg (0.03 mmol) of 2-iodo-5-methylbenzoic acid prepared by Preparation Example 3, 1.48 g (2.4 mmol) of Oxone (registered trademark) and 433 mg (3 mmol) of 5-nonanol were added to 3.75 ml of ethyl acetate, and the mixture was heated at 70° C. while being stirred for 12 hours. After being heated, the mixture was cooled to room temperature, and the insoluble substance was removed by means of filtering. Water was added to the filtrate, extraction was carried out using diethyl ether. The organic phase was dried by using sodium sulfate, and then 5-nonanone was obtained by the means of vacuum-concentration. The yield of the obtained 5-nonanone was determined and the result is shown in Table 1.

Comparative Example 2

1.57 mg (0.006 mmol) of 2-iodo-5-methylbenzoic acid prepared by Preparation Example 3, 1.11 g (1.8 mmol) of powdered Oxone (registered trademark) and 433 mg (3 mmol) of 5-nonanol were added to 3.75 ml of nitromethane, and the mixture was heated at 70° C. while being stirred for 12 hours. After being heated, the mixture was cooled to room temperature, and the insoluble substance was removed by means of filtering. Water was added in the filtrate, extraction was carried out using diethyl ether. The organic phase was dried by using sodium sulfate, and then 5-nonanone was obtained by means of vacuum-concentration. The yield of the obtained 5-nonanone was determined and the result is shown in Table 1.

Comparative Example 3

1.49 mg (0.006 mmol) of 2-iodobenzoic acid (product made in Aldrich company), 1.11 g (1.8 mmol) of powdered Oxone (registered trademark) and 433 mg (3 mmol) of 5-nonanol were added in 3.75 ml of nitromethane, and the mixture was heated at 70° C. while being stirred for 12 hours. After being heated, the mixture was cooled to room temperature, and the insoluble substance was removed by means of filtering. Water was added in the filtrate, extraction was carried out using diethyl ether. The organic phase was dried by using sodium sulfate, and then 5-nonanone was obtained by means of vacuum-concentration. The yield of the obtained 5-nonanone was determined and the result is shown in Table 1.

(Yield Determination)

The yield of the obtained carbonyl compound was determined by the following method.

The yield was obtained by weighing the obtained carbonyl compound, calculating the molar number, and calculating the yield.

Yield=(molar number of carbonyl compound)/(molar number of alcohol)×100%, wherein the molecular weight of each carbonyl compound used in calculating molar number is shown as following 5-nonanol . . . 142
benzaldehyde . . . 106
acetophenone . . . 120
5-phenylbutanoic acid . . . 164
4-phenylbutanal . . . 148
(E)-3,7-dimethylocta-2,6-dienal . . . 152
octa-7-enal . . . 154
(Z)-olealdehyde . . . 266
3,3-dimethyl-1,5-dioxaspiro[5.5]undecan-9-one . . . 198
1,4-dioxaspiro[4.5]decan-8-one . . . 156
4-(triethylsilyloxy)cyclohexanone . . . 228
6-(tert-butyldimethylsilyloxy)hexan-2-one . . . 230
3-methyl-5-(prop-1-en-2-yl)cyclohexa-2-enone . . . 150

TABLE 1

| | Example | | | | | | | | Comparative Example | | |
| --- | --- | --- | --- | --- | --- | --- | --- | --- | --- | --- | --- |
| | 1 | 2 | 3 | 4 | 5 | 6 | 7 | 8 | 1 | 2 | 3 |
| 5-Nonanol (mg) | 433 | 433 | 433 | 433 | — | — | — | 433 | 433 | 433 | 433 |
| Benzyl alcohol (mg) | — | — | — | — | 324 | — | — | — | — | — | — |
| 1-Phenylethanol (mg) | — | — | — | — | — | 367 | — | — | — | — | — |
| 4-Phenylbutanol (mg) | — | — | — | — | — | — | 450 | — | — | — | — |
| Compound (I): 2-iodobenzenesulfonic acid (mg) | 8.5 | — | — | 1.7 | — | — | — | — | — | — | — |
| Compound (I): 2-iodo-5-methylbenzenesulfonic acid (mg) | — | 8.9 | 1.8 | — | 8.9 | 8.9 | 8.9 | — | — | — | — |
| Compound (I): sodium 2-iodobenzenesulfonate (mg) | — | — | — | — | — | — | — | 9.2 | — | — | — |
| 2-Iodobenzoic acid (mg) | — | — | — | — | — | — | — | — | — | — | 1.49 |
| 2-Iodo-5-methylbenzoic acid (mg) | — | — | — | — | — | — | — | — | 7.86 | 1.57 | — |
| Oxone (registered trademark) (g) | 1.48 | 1.48 | 1.11 | 1.11 | 2.04 | 1.48 | 2.04 | 1.48 | 1.48 | 1.11 | 1.11 |
| Ethyl acetate (mL) | 3.75 | 3.75 | — | — | — | — | — | — | 3.75 | — | — |
| Acetonitrile (mL) | — | — | — | — | 3.75 | 3.75 | — | 3.75 | — | — | — |
| Nitromethane (mL) | — | — | 3.75 | 3.75 | — | — | 3.75 | — | — | 3.75 | 3.75 |
| Heating temperature (° C.) | 70 | 70 | 70 | 70 | 70 | 70 | 70 | 70 | 70 | 70 | 70 |
| Heating time (hr) | 10 | 3 | 7 | 7.5 | 1 | 1 | 6 | 3 | 12 | 12 | 12 |
| Product mass (mg) | 423 | 423 | 423 | 423 | 302 | 360 | 463 | 423 | 21 | 423 | 42 |
| Yield of product(mass %)) | 100 | 100 | 100 | 100 | 95 | 100 | 94 | 100 | 5 | 100 | 10 |

TABLE 2

| | Example | | | | | | | | |
|---|---|---|---|---|---|---|---|---|---|
| | 9 | 10 | 11 | 12 | 13 | 14 | 15 | 16 | 17 |
| 4-Phenylbutanol (mg) | 150 | — | — | — | — | — | — | — | — |
| (E)-3,7-dimethylocta-2,6-dien-1-ol (mg) | — | 154 | — | — | — | — | — | — | — |
| Octa-7-en-1-ol (mg) | — | — | 156 | — | — | — | — | — | — |
| (Z)-octadeca-9-en-1-ol (mg) | — | — | — | 268 | — | — | — | — | — |
| 3,3-dimethyl-1,5-dioxaspiro[5.5]undecan-9-ol (mg) | — | — | — | — | 200 | — | — | — | — |
| 1,4-dioxaspiro[4.5]decane-8-ol (mg) | — | — | — | — | — | 158 | — | — | — |
| 4-(triethylsilyloxy)cyclohexanol (mg) | — | — | — | — | — | — | 230 | — | — |
| 6-(tert-butyldimethylsilyloxy) hexan-2-ol (mg) | — | — | — | — | — | — | — | 232 | — |
| 3-methyl-5-(prop-1-en-2-yl) cyclohexa-2-enol (mg) | — | — | — | — | — | — | — | — | 152 |
| Compound (I): sodium 2-iodobenzenesulfonate (mg) | 6.1 | 6.1 | 6.1 | 6.1 | 6.1 | 6.1 | 6.1 | 6.1 | 6.1 |
| Oxone (registered trademark) (g) | 0.37 | 0.37 | 0.37 | 0.37 | 0.49 | 0.49 | 0.49 | 0.49 | 0.49 |
| Sodium sulfate anhydrous (g) | 0.5 | 0.5 | 0.5 | 0.5 | 0.5 | 0.5 | 0.5 | 0.5 | 0.5 |
| Ethyl acetate (mL) | — | — | — | — | 5 | 5 | 5 | 5 | 5 |
| Nitromethane (mL) | 5 | 5 | 5 | 5 | — | — | — | — | — |
| Heating temperature (° C.) | 70 | 70 | 70 | 70 | 70 | 70 | 70 | 70 | 70 |
| Heating time (hr) | 2 | 2 | 2 | 2 | 8 | 8 | 8 | 7 | 8 |
| Yield of product (mass %) | 91 | — | 92 | 90 | 91 | 86 | 74 | 90 | 91 |
| Yield of product (E/Z) | — | 16 | — | — | — | — | — | — | — |

From the results of Table 1 and Table 2, the yield of carbonyl compounds in Examples 1 to 17, in which alcohol were oxidized in the presence of Compound (I) and Oxone (registered trademark) as an oxidant, have high values.

On the other hand, in Comparative Example 1-3 in which Compound (I) was not added, the yield of carbonyl compound was high only in Comparative Example 2 in which nitromethane was used as solvent in the presence of 2-iodo-5-methylbenzoic acid. However, in Comparative Example 1 in which ethyl acetate was used as a solvent, even if addition amounts of 2-iodo-5-methylbenzoic acid increased, the yield decreased. In addition, the yield was low in the presence of 2-iodobenzoic acid even if nitromethane was used as solvent.

In contrast, in Examples 1 to 17, the carbonyl compounds were obtained at higher yields even if solvents other than nitromethane were used.

In addition, Examples 3 to 7 in which Oxone (registered trademark) was powdered showed higher yields even if the shorter heating time was used in comparison with Example 1.

In addition, in Example 9-12 in which primary alcohol was used, an aldehyde compound was prepared selectively by adding anhydrous sodium sulfate as a dehydrating agent.

Example 18-27

2-Iodobenzenesulfonic acid sodium salt prepared by Preparation Example 4 powdered Oxone (registered trademark), ten kinds of cycloalkanols as shown in Table 3 were added in nitromethane and the mixture was heated at 70° C. while being stirred under nitrogen for 6-24 hours. The later treatments were carried out in the same way as in Example 1, and then cycloenones were obtained. The yields of the obtained cycloenones were determined and the results are shown in Table 3.

TABLE 3

| | Example | | | | | | |
|---|---|---|---|---|---|---|---|
| | 18 | 19 | 20 | 21 | 22 | 23 | 24 |
| Cycloalkanol (0.2 mmol) | cyclohexanol (OH) | 4-t-Bu-cyclohexanol | cyclopentanol (OH) | cyclohexenol | 4-Me-cyclohexanol | 4-Ph-cyclohexanol | 4-OTBDPS-cyclohexanol |
| Cycloenone | cyclohex-2-enone | 4-t-Bu-cyclohex-2-enone | cyclopent-2-enone | cyclohex-2-enone | 4-Me-cyclohex-2-enone | 4-Ph-cyclohex-2-enone | 4-OTBDPS-cyclohex-2-enone |

TABLE 3-continued

| | | | | | | | |
|---|---|---|---|---|---|---|---|
| Compound (I): sodium 2-iodobenzenesulfonate (mg) (0.01 mmol) | 3.1 | 3.1 | 3.1 | 3.1 | 3.1 | 3.1 | 3.1 |
| Oxone (registered trademark) (g) (0.4-0.6 mmol) | 0.246 | 0.308 | 0.246 | 0.246 | 0.246 | 0.246 | 0.246 |
| Nitromethane (mL) | 1 | 1 | 1 | 1 | 1 | 1 | 1 |
| Heating temperature (° C.) | 70 | 70 | 70 | 70 | 70 | 70 | 70 |
| Heating time (hr) | 5 | 8 | 24 | 8 | 8 | 6 | 8 |
| Yield of product (mass %) | 91 | 82 | 70 | 83 | 88 | 88 | 61 |

| | Example | | |
|---|---|---|---|
| | 25 | 26 | 27 |
| Cycloalkanol (0.2 mmol) | (structures shown) | | |
| Cycloenone | (structures shown, 78% (4:1)) | | |
| Compound (I): sodium 2-iodobenzenesulfonate (mg) (0.01 mmol) | 3.1 | 3.1 | 3.1 |
| Oxone (registered trademark) (g) (0.4-0.6 mmol) | 0.369 | 0.246 | 0.308 |
| Nitromethane (mL) | 1 | 1 | 1 |
| Heating temperature (° C.) | 70 | 70 | 70 |
| Heating time (hr) | 12 | 12 | 24 |
| Yield of product (mass %) | 78 | 78 | 74 |

INDUSTRIAL APPLICABILITY

According to the present invention, a carbonyl compound, which is an extremely important material in organic synthesis, can be prepared in highly efficiently by the oxidation process for preparation of alcohol, even when using a solvent which is easy to handle.

The invention claimed is:

1. A process for the preparation of a carbonyl compound, comprising a step of:
    oxidizing an alcohol in at least one solvent selected from the group consisting of an ester solvent, a nitrile solvent, a halogen solvent, an aromatic solvent, a ketone solvent, an ether solvent, and a nitroalkane solvent, in the presence of an oxidant and a 2-iodobenzenesulfonic acid represented by formula (I) or a salt thereof,

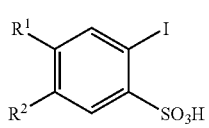

(I)

wherein $R^1$ and $R^2$ independently represent hydrogen, a halogen, an alkyl or an alkoxy group, each of which optionally has a substituent, or $R^1$ and $R^2$ combine the two carbon atoms to which they are bonded to form an aromatic ring, the carbonyl compound is an aldehyde, ketone, carboxylic acid, ester or lactone, and the oxidant is a peroxymonosulfuric acid salt.

2. The process for the preparation of a carbonyl compound according to claim 1, wherein $R^1$ is hydrogen, and $R^2$ is an alkyl group having 1-4 carbon atoms.

3. The process for the preparation of a carbonyl compound according to claim 1, wherein $R^1$ and $R^2$ are each hydrogen.

4. The process for the preparation of a carbonyl compound according to claim 1, wherein the oxidant is a mixture of inorganic salts of potassium hydrogen peroxysulfate, potassium hydrogen sulfate, and potassium sulfate.

5. The process for the preparation of a carbonyl compound according to claim 1, wherein said oxidation occurs in the presence of a dehydrating agent.

6. The process for the preparation of a carbonyl compound according to claim 5, wherein the dehydrating agent is anhydrous sodium sulfate.

7. The process for the preparation of a carbonyl compound according to claim 1, wherein the alcohol is a cyclic secondary alcohol with a 5-12 membered ring which may have a substituent, and the carbonyl compound is a cyclic α,β-enone with a 5-12 membered ring which may have a substituent.

8. A process for the preparation of a carbonyl compound, comprising steps of:

preparing a liquid admixture comprising (i) an oxidant and (ii) a 2-iodobenzenesulfonic acid represented by formula (1) or a salt thereof

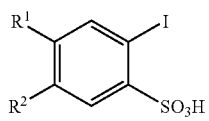

(I)

said liquid admixture further comprising (iii) alcohol and (iv) at least one solvent selected from the group consisting of an ester solvent, a nitrile solvent, a halogen solvent, an aromatic solvent, a ketone solvent, an ether solvent, and a nitroalkane solvent; and heating the liquid admixture, wherein $R^1$ and $R^2$ independently represent hydrogen, a halogen, or an alkyl or alkoxy group, each of which optionally has a substituent, or $R^1$ and $R^2$ combine the two carbon atoms to which they are bonded to form an aromatic ring, the carbonyl compound is an aldehyde, ketone, carboxylic acid, ester or lactone, and the oxidant is a peroxymonosulfuric acid salt.

9. The process for the preparation of a carbonyl compound according to claim 8, wherein $R^1$ is hydrogen, and $R^2$ is an alkyl group having 1-4 carbon atoms.

10. The process for the preparation of a carbonyl compound according to claim 8, wherein $R^1$ and $R^2$ are hydrogens.

11. The process for the preparation of a carbonyl compound according to claim 8, wherein the oxidant is a mixture of inorganic salts of potassium hydrogen peroxysulfate, potassium hydrogen sulfate, and potassium sulfate.

12. The process for the preparation of a carbonyl compound according claim 8, wherein said oxidation occurs in the presence of a dehydrating agent.

13. The process for the preparation of a carbonyl compound according to claim 12, wherein the dehydrating agent is anhydrous sodium sulfate.

14. The process for the preparation of a carbonyl compound according to claim 8, wherein the alcohol is a cyclic secondary alcohol with a 5-12 membered ring which may have a substituent, and the carbonyl compound is a cyclic α,β-enone with a 5-12 membered ring which may have a substituent.

15. The process for the preparation of a carbonyl compound according to claim 1, wherein the alcohol is represented by formula (II)

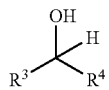

(II)

wherein $R^3$ and $R^4$ are optionally substituted moieties that are independently selected from the group consisting of alkyl, alkenyl, alkynyl, cycloalkyl, cycloalkenyl, aryl and heteroaryl, or $R^3$ and $R^4$ combine with the carbon to which they are bonded to form cycloalkyl or cycloalkenyl; and the carbonyl compound is represented by formula (III)

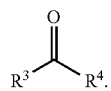

(III)

16. The process for the preparation of a carbonyl compound according to claim 1, wherein the alcohol is 5-nonanol.

17. The process for the preparation of a carbonyl compound according to claim 1, wherein the solvent is acetonitrile.

18. The process for the preparation of a carbonyl compound according to claim 8, wherein the alcohol is represented by formula (II)

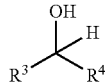

(II)

wherein $R^3$ and $R^4$ are optionally substituted moieties that are independently selected from the group consisting of alkyl, alkenyl, alkynyl, cycloalkyl, cycloalkenyl, aryl and heteroaryl, or $R^3$ and $R^4$ combine with the carbon to which they are bonded to form cycloalkyl or cycloalkenyl; and the carbonyl compound is represented by formula (III)

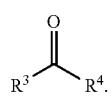

(III)

19. The process for the preparation of a carbonyl compound according to claim 8, wherein the alcohol is 5-nonanol.

20. The process for the preparation of a carbonyl compound according to claim 8, wherein the solvent is acetonitrile.

* * * * *

UNITED STATES PATENT AND TRADEMARK OFFICE
CERTIFICATE OF CORRECTION

| | |
|---|---|
| PATENT NO. | : 8,394,995 B2 |
| APPLICATION NO. | : 12/441194 |
| DATED | : March 12, 2013 |
| INVENTOR(S) | : Ishihara et al. |

Page 1 of 2

It is certified that error appears in the above-identified patent and that said Letters Patent is hereby corrected as shown below:

ON TITLE PAGE, ITEM [57]:

Line 10, "boned" should read --bonded--.

IN THE SPECIFICATION:

COLUMN 2:

Line 12, "boned" should read --bonded--;

Line 56, "exists" should read --exists.--; and

Line 59, "sulfate" should read --sulfate.--.

COLUMN 3:

Line 12, "boned" should read --bonded--.

COLUMN 4:

Line 9, "boned" should read --bonded--;

Line 20, "a" should read --an--;

Line 44, "hydrogen." should read --hydrogen is selected.--; and

Line 63, "become" should read --becomes--.

Signed and Sealed this
Twenty-fifth Day of March, 2014

Michelle K. Lee
*Deputy Director of the United States Patent and Trademark Office*

COLUMN 8:

Line 46, "boned" should read --bonded--.

COLUMN 13:

Line 26, "under a nitrogen" should read --under nitrogen--;

Line 40, "under a nitrogen" should read --under nitrogen--;

Line 54, "under a nitrogen" should read --under nitrogen--; and

Line 67, "under a" should read --under--.

COLUMN 14:

Line 14, "under a nitrogen" should read --under nitrogen--;

Line 29, "a nitrogen" should read --nitrogen--;

Line 43, "a nitrogen" should read --nitrogen--; and

Line 57, "under a nitrogen" should read --under nitrogen--.

COLUMN 15:

Line 5, "under a nitrogen" should read --under nitrogen--.

COLUMN 17:

Line 26, "were" should read --was--; and

Line 28, "have" should read --has--.

COLUMN 19:

Line 56, "in" should be deleted.